US007728280B2

(12) United States Patent
Feilkas et al.

(10) Patent No.: US 7,728,280 B2
(45) Date of Patent: Jun. 1, 2010

(54) MULTI-BAND TRACKING AND CALIBRATION SYSTEM

(75) Inventors: Thomas Feilkas, Grafing (DE); Manfred Weiser, München (DE)

(73) Assignee: BrainLAB AG, Feldkirchen (DE)

( * ) Notice: Subject to any disclaimer, the term of this patent is extended or adjusted under 35 U.S.C. 154(b) by 57 days.

(21) Appl. No.: 11/954,125

(22) Filed: Dec. 11, 2007

(65) Prior Publication Data

US 2008/0135733 A1  Jun. 12, 2008

Related U.S. Application Data

(60) Provisional application No. 60/882,750, filed on Dec. 29, 2006.

(30) Foreign Application Priority Data

Dec. 11, 2006  (EP)  .................................. 06025561

(51) Int. Cl.
*H01L 27/00* (2006.01)
(52) U.S. Cl. ..................................... 250/216; 250/208.1
(58) Field of Classification Search .................. 250/226, 250/208.1; 348/262, 263, 265
See application file for complete search history.

(56) References Cited

U.S. PATENT DOCUMENTS 4,896,673 A * 1/1990 Rose et al. ................... 600/439
5,703,357 A * 12/1997 Shih et al. ................... 250/226
6,428,547 B1   8/2002 Vilsmeier et al.
6,724,922 B1   4/2004 Vilsmeier
2003/0135092 A1   7/2003 Cline et al.
2003/0208125 A1  11/2003 Watkins
2004/0002642 A1   1/2004 Dekel et al.
2005/0179807 A1*  8/2005 Lin ............................. 348/344
2005/0285038 A1* 12/2005 Frangioni .................... 250/330
2007/0115376 A1*  5/2007 Igarashi ....................... 348/262
2007/0188650 A1*  8/2007 Kobayashi et al. ........... 348/344

FOREIGN PATENT DOCUMENTS

| DE | 199 44 516 | 4/2001 |
|---|---|---|
| EP | 1 138 256 | 10/2001 |
| EP | 1 413 258 | 4/2004 |
| EP | 1 554 987 | 7/2005 |
| EP | 1 667 067 | 6/2006 |
| WO | 96/41481 | 12/1996 |
| WO | 99/17133 | 4/1999 |
| WO | 99/30182 | 6/1999 |
| WO | 01/01854 | 1/2001 |

* cited by examiner

*Primary Examiner*—Georgia Y Epps
*Assistant Examiner*—Tony Ko
(74) *Attorney, Agent, or Firm*—Renner, Otto, Boisselle & Sklar, LLP (57) ABSTRACT

A camera system includes at least two camera units, wherein each camera unit comprises at least one detection element for detecting an optical signal. At least one of the at least two camera units includes at least one element operative to enable detection of light in at least two different spectral ranges.

15 Claims, 5 Drawing Sheets

MULTI-BAND TRACKING AND CALIBRATION SYSTEM

RELATED APPLICATION DATA

This application claims priority of U.S. Provisional Application No. 60/882,750 filed on Dec. 29, 2006, which is incorporated herein by reference in its entirety.

FIELD OF THE INVENTION

The present invention relates to a multi-band tracking, calibration and/or registration system for calibrating, detecting and/or registering an object such as an instrument (e.g., a medical instrument), implant, patient and/or structure.

BACKGROUND OF THE INVENTION

In order to use a medical instrument in image-guided surgery, the instrument has to be calibrated, verified and/or validated, i.e., the dimensions, configuration and/or arrangement of the instrument are made known to a navigation system or the like. Otherwise, for example, if the instrument is damaged (e.g., bent), healthy tissue that lies next to tissue to be treated may be impinged by the instrument.

A device and method for calibrating a bent element are known from EP 1 413 258 A1, wherein the bent element is connected to a navigation element, placed onto a calibrating device, and moved while resting on said calibrating device until the element is calibrated.

The navigational calibration of medical instruments or implants is known from EP 1 369 090 A1. A spatial position of the instrument or implant is ascertained by means of a medical navigation system. This enables the relative position of the instrument or implant to be ascertained with respect to anatomical data, wherein the spatial orientation of a multi-dimensionally configured, functional section of the instrument or implant can be ascertained.

U.S. Pat. No. 6,428,547 B1 describes detecting the shape of a treatment device, wherein the treatment device is referenced in a computer-controlled, camera-assisted navigation system by means of a marker array attached to the treatment device. Projections of the treatment device can be detected by means of radiographic images, and, in the navigation system, the shape of the treatment device can be assigned to the projections via the position of the marker array in/on the projections.

A verification method for positions in camera images is known from U.S. Pat. No. 6,724,922 B1.

DE 199 44 516 A1 describes a method for detecting a shape of an object, wherein a camera image of the object is produced and an outline of the object is detected in a first plane by an evaluation unit (which is connected to the camera). The focusing distance of the camera is changed and an outline of the object is detected in a second plane by the evaluation unit. These steps are repeated until a sufficient number of outlines have been detected, such that the spatial shape of the object can be determined.

EP 1 667 067 A1 discloses a method for calibrating an instrument or implant to which at least one marker is attached. The position of the instrument or implant in space can be determined using the at least one marker. Outlines, a view and/or a geometry of the instrument or implant can be optically captured from at least one side and compared with corresponding outlines, views and/or geometries of stored pre-calibration data of the instrument or implant. A determination then can be made whether or not the instrument or implant is calibrated. A device for calibrating an instrument or implant includes a computational unit connected to a memory in which pre-calibration data of the instrument are stored; at least one camera, using which markers attached to the instrument can be captured; and at least one video camera, wherein the at least one camera and the video camera are connected to the computational unit and exhibit a defined positional relationship to each other. The positional relationship can be determined by the computational unit, and the image data of the instrument as captured by the video camera can be evaluated using the instrument position information as captured by the camera, such that said data can be compared with the pre-calibration data.

A system for determining the spatial position of a body is known from WO 99/17133 and WO 99/30182.

SUMMARY OF THE INVENTION

A camera system in accordance with the invention comprises at least two optical detection systems or cameras arranged, for example, within a casing and being separated from one another by a predetermined distance (e.g., 10 to 1000 mm). At least one and advantageously each optical detection system can be designed such that light may be simultaneously or sequentially detected in a different spectral or wavelength range. These ranges can include, for example, infrared, visible light (for example in the range of about 380 to about 780 nm) and light having a wavelength in the ultraviolet range. On the one hand, this enables a tracking method to be performed using the camera system in conjunction with a navigation system such as is known in its own right, wherein, for example, the cameras or detection system detect light in the infrared range. On the other hand, the detection system or cameras, for example, also can be used to detect light in the visible range. This enables calibration, verification and/or validation of an instrument. By integrating at least two detection devices for detecting light, such as visible light, into the cameras for detecting other types of light (e.g., infrared light) of a known stereoscopic camera system, it is possible (without significantly increasing the weight of the camera system as a whole and without set-up or synchronization problems) to easily provide a device that can not only be used to track markers that reflect, for example, infrared light, but also enables the evaluation of optical information, for example in the visible wavelength range.

The camera system in accordance with the invention also can be used in place of known camera systems that, for example, only detect infrared light, wherein this functionality is retained and broadened to include optical detection in another wavelength range. This additional capability can be used, for example, to perform calibration by means of stereoscopic recordings.

Where wavelength or spectral ranges are mentioned herein, this is intended to encompass light of a constant wavelength.

A camera can be modified to detect light of another, different wavelength range, for example, by providing a beam splitter. Such beam splitter may be a prism or semi-transparent mirror, for example, which can lie in the beam path of light entering a lens or lens system. The incident light split by the beam splitter, after the beam has been split, can strike (e.g., impinge on) a detection element such as a first sensor. The sensor, for example, can be a known CCD array for detecting light of a first wavelength range. The split beam also can impinge on a second sensor for detecting light of a second, different wavelength range. A system for separating incident light is for example described in WO 96/41481 and, in particular, in the example embodiment shown in FIG. 7 of WO 96/41481. The content of WO 96/41481 is hereby incorporated by reference in its entirety.

The term "detection element" or "CCD element" includes any detection element for detecting an optical signal and, for example, converted into an electrical signal, such as for example a separate camera, a CCD chip, CMOS sensor or the like.

It is noted that it is also possible to provide more than two detection elements or CCD elements in an individual camera to enable detection of more than two spectral ranges. Additional semi-transparent mirrors and/or prisms and optionally also additional filter elements, for example, can be used in the cameras to simultaneously or sequentially detect ultraviolet light, visible light and infrared light.

It is also possible to use one or more optical filters positioned in front of one or more detection elements, for example a CCD array, or positioned in the beam path of the light reaching the respective detection element. This can enable light of different wavelengths to be detected by different sensors of the same or different constructions. It is also possible to use sensors that are respectively formed to specifically detect a particular wavelength range. If, for example, only one detection element (e.g., a CCD array) is provided for each camera of the camera system, then it may be made possible to detect light of different wavelength ranges. For example an optical filter that only passes light of a first wavelength range can be arranged in front of the detection element or in the beam path of the light that impinges on the detection element. As a result, only light of the first wavelength range can be detected by the detection element. After a predetermined period of time, in which the light of the first wavelength range has been detected, the filter can be removed or replaced by another filter at the same location or also for example at a different location, in order to detect light of a second wavelength range.

A filter such as a passive filter element can be used wherein the filter characteristics are fixed (e.g., a color filter). Alternatively, an active filter whose filter characteristics can be controlled may be used (e.g., a polarization filter).

It is also possible to provide a camera system, for example, wherein the system includes a movable mirror that in a first position deflects light onto a first detection element, and in a second, for example folded-away or rotated position, deflects light onto a second detection element. The movable mirror can be constructed, for example, as in a single lens reflex (SLR) camera such as is known in its own right. Further, depending on the desired wavelength range to be detected, the mirror can be moved by a mechanism such as is known from an SLR camera so as to deflect light impinging on the mirror and then onto the respective sensor.

The frame rate at which a camera detects light of different wavelengths (e.g., sequential detection), for example, can lie in the range of 50 ms per frame. Thus, in one second ten frames are detected in a first wavelength range and ten frames are detected in a second, different wavelength range.

Since the same lens system, through which light enters the camera, can be used in all of the embodiments of the camera system as described herein, it is possible to determine the corresponding pixels, e.g., a pixel-to-pixel relationship, between the two imaging modalities. The transformation protocol for mapping a pixel in a first image, e.g., an infrared image, onto a corresponding second image, e.g., an image in the visible range, can be known or determined such that it is possible to determine a location on the medical instrument (which is clearly identifiable in the visible range) that the markers (which are clearly visible in the infrared range) are arranged, so as to be able to track and simultaneously also calibrate the instrument. Ideally, the respective pixels of an image recorded in a first wavelength range, for example, can be directly mapped onto the corresponding pixel of an image recorded in a second, different wavelength range. Then, the images in two different wavelength ranges, detected by the same detection element or by two different detection elements, can be superimposed to provide the combined information from detecting both wavelength ranges in one image.

As opposed to the use of external image sources, a synchronization method does not have to be performed for the camera system in accordance with the invention. Since synchronizing the individual sub-assemblies or partial elements of the camera, such as for example the movable mirror or filters or different detection elements, has already been solved by hardware, firmware, software settings and/or adjustments during or after manufacture of the camera system, subsequent synchronization is not required. Thus, when using the camera system for navigation, corresponding stereo video images can be provided, fully synchronized, in addition to tracking the infrared markers. To this end, the camera system merely needs to be calibrated, which, for example, can be performed before it is used for the first time, e.g., by detecting two test images and then comparing the two test images to determine the aforementioned transformation protocol.

Using the camera system in accordance with the invention, it is thus possible for example to verify an instrument in a non-contact process, wherein as opposed to known methods, the use of a calibrating instrument, such as for example an instrument calibration matrix (ICM), can be omitted.

A model of the three-dimensional surface of an object also can be reconstructed from the at least two recordings of the object, as for example described in the article "Shape from Stereo Using Fine Correlation: Method and Error Analysis" by Frédéric Devernay and Olivier Faugeras, which is hereby incorporated by reference in its entirety.

One or more light sources, such as for example LEDs, lasers or lamps, can advantageously be arranged on one or more cameras, for example around an incident light opening or lens of the cameras. The light sources on the cameras can be advantageously designed such that light is emitted in at least one of the wavelength ranges detectable by the camera system, such as for example infrared light, and this emitted light, for example, is reflected from reflective surfaces (e.g., a marker) and transmitted back to the camera. It is also possible to provide light sources of different types on one camera, such as for example lamps for emitting visible light, LEDs or lasers. If a laser or video projector, for example, is used as a light-emitting or projection element, then reconstructing three-dimensional surfaces can be simplified by using so-called "structured light", as described in the article "3-D Computer Vision Using Structured Light: Design, Calibration and Implementation Issues" by Fred W. DePiero and Mohan M. Trivedi, in: Advances in Computers, Volume 43, pages 243 to 278, depiero96computer, 1996.

A lens system lying in front of the respective detection elements of the camera can be provided as a variable lens system, in order to perform setting procedures such as for example zooming or focusing, as also known from photography. The variable lens system, for example, can be set manually or electronically, in order to configure the camera system to optimally detect an object at a predetermined distance from the camera system.

A computational unit is preferably connected to both cameras and can contain the images recorded by the respective cameras. The computational unit also can process and/or evaluate the images as stereo images, for example, to perform a calibration after performing a 3D reconstruction method.

It is also optionally possible to use three or more cameras that preferably are designed such that light can be detected in at least two different wavelength ranges.

In accordance with another aspect of the invention, there is provided a navigation system comprising a camera system as described herein.

A device for calibrating an instrument that preferably can be used medically and to which at least one marker or reference star is attached, includes a computational unit and a memory connected to the device, wherein pre-calibration data of at least one medical instrument are stored in the memory. At least one camera, as described herein, is also provided for detecting markers attached to the instrument (e.g., by means of reflected infrared light). The camera can be connected to the computational unit, which can ascertain the spatial position of the instrument on the basis of the detected marker image data and optionally on the basis of the pre-calibration data. The device also can include a second camera or image detecting device that is integrated into the above-described camera and can detect light of another wavelength range, which cannot for example be detected by the above-described camera. Using the second camera, the instrument itself or the geometry or dimensions of partial regions of the instrument can be detected, wherein the second camera is also connected to the computational unit. A comparison then can be made in the computational unit between the instrument data optically detected by the camera and the pre-calibration data stored in the memory, wherein the camera for detecting the marker positions is identical to the camera for optically detecting the instrument. It is also possible to detect the position of the markers using the same camera and so as to track the instrument connected to the markers, and to detect the instrument itself or its dimensions.

The invention also relates to a system comprising a device as described above and an instrument to which at least one marker is attached.

In a method in accordance with the invention for calibrating, verifying or validating an instrument or implant (also referred to below as the instrument) which can preferably be used medically and to which at least one marker (and preferably three markers, for example in the form of a so-called reference star, or a number of markers having a geometry which is known, fixed or for example variable depending on the configuration of the instrument) is attached. The position of the instrument in space can be ascertained in a known way by means of a navigation system, for example, using an infrared stereo camera. and markers, which can be formed as reflective surfaces or spheres. For detecting the position of the instrument, a camera can be provided that is integrated into at least one infrared camera and, for example, can detect visible light emitted or reflected by the instrument. The camera is preferably calibrated and the position of the camera in space is also known or defined. The geometry, e.g., one or more views, images or outlines of the instrument from one direction or from different directions, also can be optically detected by means of at least one camera. The camera can be the same camera used to detect the position of the markers, or can also be a second camera, different from said camera, so as to record images in the visible wavelength range, for example.

The geometry or calibration data of the instrument can be stored in software or a computer, such that the three-dimensional representation of the instrument, for example, is stored in a database. These stored, so-called pre-calibration data can be compared with the geometry of the instrument as detected by the camera. This comparison can be used with the optical detection data to determine whether the optically detected data representing the actual geometry or configuration of the instrument match the pre-calibration data. So-called tracking data, detected for example in the infrared range, and a camera image detected in the visible range are thus assigned, wherein if the camera image data match the pre-calibration data, the instrument is said to be in calibration, verified and/or validated. If a difference or deviation from the pre-calibration data is determined, an error prompt, for example, can be output such that the instrument has to be calibrated or the pre-calibration data used for subsequent navigation have to be adjusted to the optical detection data. Preferably, those views or outlines of the instrument model that correspond to the orientation or relative position between the actual instrument and the camera as measured by means of the markers are respectively calculated from a three-dimensional data or software model of the instrument.

If it is assumed that the image calculated by the computer on the basis of the detected position in space of the instrument (which is known as a three-dimensional model) and on the basis of the knowledge of the calibration of the video camera (which is the representation, view, model of the world, or of an instrument by the computer or a software), and that the video input data detected by the camera show the situation in the real world (e.g., an actual available instrument), then if the video camera is properly calibrated (the camera has a known position and orientation and detection range) and the medical instrument is registered or calibrated, the image calculated by the computer would coincide, for a pre-calibrated instrument, with the image which is seen in the video input. If this is not the case, then either the calibration or adjustment of the camera is faulty or the instrument does not correspond to the pre-calibration data, for example, because it is bent. If it is assumed that the calibration of the camera is correct throughout the method, then instruments for which pre-calibration data are available can be reliably verified using the calibrated volume which can be detected by the camera.

The data stored for example in a computer, which define the geometry and optionally also possible degrees of freedom of the instrument, can be stored in a database or the like as pre-calibration data (e.g., as a description of the three-dimensional object) for a navigation system. The data can represent a three-dimensional model that describes the exact shape of an object or instrument and the position of each marker or reference array on the object. The navigation system or a computer can display the three-dimensional model that corresponds to the instrument the surgeon is using. The description of the pre-calibrated instrument, for example, can include information as to which regions, functional locations or areas of the instrument have to be verified. It is also possible to store, as pre-calibration data, information that defines possible shapes that the instrument can assume, such as for example information regarding joints that the instrument may have and ways in which such joints can move, or in general information regarding ways in which the instrument may change or its degrees of freedom.

A calibrated video signal is an input that, for example, can be received from a standard video camera. The properties or parameters of the signal, such as for example the position and/or detection function of the camera, can be determined and calculated for a so-called "virtual" camera. This virtual camera can be used by the computer to calculate images based on three-dimensional objects. This can be accomplished, for example, by projecting in the detection direction of the actual camera, which match the views or objects actually available or detected, such that when the video camera is pointed at a cube-shaped object of known dimensions, the position of the cube-shaped object in three-dimensional space, once the camera volume has been calibrated, can be determined on the basis of the image information. Additional information then can be superimposed onto the video image recorded by the camera, for example, such that this additional information (e.g., a virtual representation of the instrument to be verified) looks like a part of the scene recorded by the camera.

The calibrated video signal can be used to verify and validate pre-calibrated instruments, wherein it is not necessary to use any other object, such as for example a contact area, such that the surgeon's working range is not restricted by an additional object or instrument. Verification, which can be a non-contact process, merely requires a surgeon to hold the instrument to be calibrated such that the video camera can detect at least a partial outline or record a partial view of the object from at least one side. A subsequent software application, such as for example navigation software of the navigation system, can automatically determine whether the detected shape is correct by comparing it with the pre-calibration data.

If an instrument having a more complex shape is to be calibrated, the instrument may be moved or rotated so as to record a number of views of the instrument via the camera, wherein the software, for example, can output a corresponding instruction to move the instrument. Optionally or additionally, other cameras can also be provided to enable detection of the instrument from different directions.

Using the method in accordance with the invention, it is possible to ensure that only calibrated instruments or implants are used for surgical methods. More specifically, if, for example, the shape of an instrument to be used deviates from the pre-calibration data, an error prompt can be output, or the navigation system may not enable the instrument, which has been identified as faulty, to be navigated.

Since it is no longer necessary, in accordance with the invention, to place an instrument to be calibrated onto a reference area, the handling of instruments which are to be kept sterile is simplified.

Preferably, not only one but at least two or more lateral views of the instrument are detected in the visible range of light by an optical camera, wherein the instrument can also be rotated or shifted within the visual range of the camera. Preferably, the visibility of particular points, such as for example the tip of an instrument, can be tested. To this end, it is for example possible to test whether specific points defined in the pre-calibration data, such as for example corner points, edges or tips of the instrument, are also visible or are obscured in the optically detected recording. If obscured, a signal can be output in order to indicate to a user that he should hold and/or reposition the instrument, unobstructed, in the line of sight of the camera.

It is also possible for only particular regions, such as for example corner points, edges, a tip or functional areas, of the instrument which are characteristic of or relevant to the function of the instrument to be tested relative to the pre-calibration data. Information in this respect can be stored in software and, for example, in the pre-calibration data.

In general, the pre-calibration data can include information on the geometry, dimensions, the spatial arrangement of combinable elements (e.g., an instrument and exchangeable tips or an instrument for positioning implants in conjunction with the selected implant) and/or on possible degrees of freedom (e.g., joints or ways of deforming the instrument). By using the pre-calibration data, the configuration or the current state of an instrument, which may be adjusted or deformed, can be identified so as to subsequently use this information on the actual configuration of the instrument, e.g., within the framework of treatment assistance or for a surgical incision by means of image-guided surgery.

Comparing the image data detected by the camera with the pre-calibration data can also be used to test whether an instrument is within a predetermined specification. This predetermined specification, for example, can be specified in the pre-calibration data as a tolerance regarding the dimensions of the instrument. If it is determined that an instrument exceeds a tolerance limit, a corresponding prompt, for example, can be output.

The data, recorded by the camera, regarding the actual state or configuration of the instrument can also be used to adapt or modify the pre-calibration data, such that the data regarding the actual configuration of an instrument, as ascertained by means of the camera, can for example be provided to a navigation system, in order to precisely navigate said instrument.

An instrument corresponding to the pre-calibration data and/or an instrument actually detected by the camera, for example, can be indicated on a screen. It is also possible for both instruments, e.g., the actual and the virtual instrument, to be simultaneously indicated adjacent to one another or superimposed on one another, for example as a so-called overlap image. Characteristic points such as corners and/or edges then can be compared to determine whether the actual instrument matches the virtual instrument in accordance with the pre-calibration data or deviates from it.

The camera for optically detecting the instrument in the visible range is preferably calibrated. To this end, an optical pattern such as for example a chessboard or an object having known dimensions can be held in front of a camera, for example, such that on the basis of the image data detected by the camera, the dimensions of an object situated within the visual range of the camera can be ascertained, optionally using navigation data.

In accordance with another aspect of the invention, there is provided a computer program which, when it is loaded onto a computer or is running on a computer, performs one or more of the method steps described herein. The program can include, for example, program sections for evaluating image data detected by an optical camera such that dimensions or the geometry of a visible region of the instrument can be determined, optionally using navigation data, wherein the optically detected data can be compared with pre-calibration data. The computer program may be provided on a program storage medium or as a computer program product.

BRIEF DESCRIPTION OF THE DRAWINGS

The forgoing and other features of the invention are hereinafter discussed with reference to the drawings.

DETAILED DESCRIPTION

Figure 1:
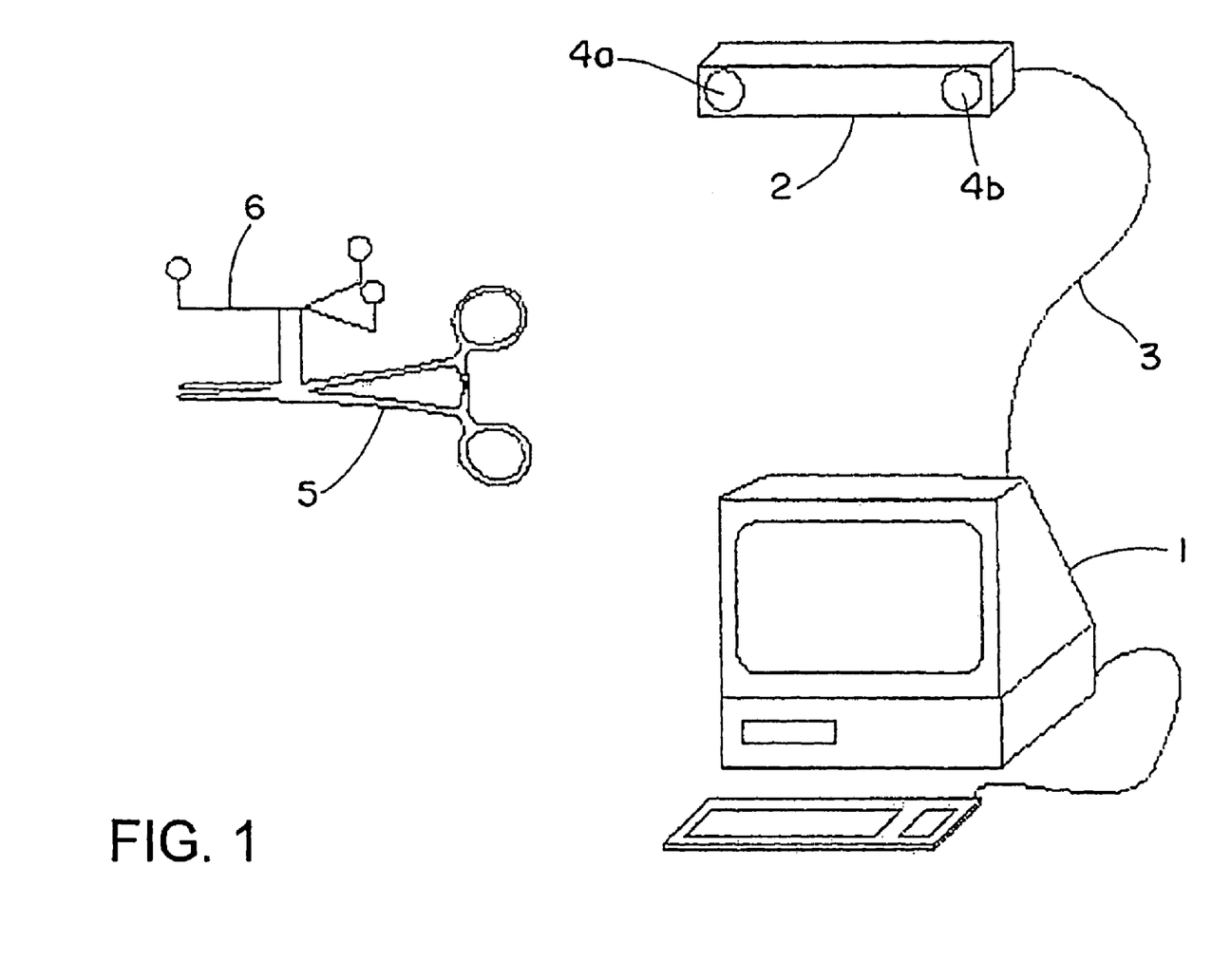
FIG. 1 illustrates an exemplary device in accordance with the invention.

FIG. 1 shows a first exemplary navigation system 1 in accordance with the invention, wherein the navigation system 1 is coupled to an optical camera comprising two individual cameras 4a and 4b, which are part of an optical tracking system 2 and are describe din more detail below. The navigation system 1 can be connected to the optical tracking system 2 by means of a data line, such as for example a cable 3, or via radio. The cameras 4a and 4b can detect infrared light signals emitted or reflected by markers (e.g., the three markers of the reference star 6) so as to detect a position of the medical instrument 5 (shown as a pair of scissors) connected to the reference star 6. Each of the cameras 4a and 4b also can be used as a video camera, wherein visible light is detected. The data of the reference star 6, detected by the optical tracking system 2 in the infrared mode of the cameras 4a and 4b, can be transmitted to the computational unit 1, together with the data of the instrument 5 detected in the video camera mode, and for example evaluated as described in EP 1 667 067 A1 by referring to FIG. 3 and 4 in EP 1 667 067 A1.

By integrating the video camera function into the optical infrared tracking system, the step of calculating the current position of the video cameras in space is omitted. Thus, an instrument 5, which, for example, may be pre-calibrated, can be tested or verified by correlating the images recorded by the cameras 4a and 4b in the infrared range for detecting the markers and in the visible range for detecting the shape or geometry of the instrument 5. This data can be used to determine if there is a deviation of the instrument from a predetermined shape of the instrument. Calibrating the video cameras, for example when manufacturing the system, provides the information for a "virtual camera". This information remains valid, since the position of the video camera relative to the tracking system is not changed after calibration. If another, detached video camera 4c is provided, as shown in FIG. 2, then the current position of the camera 4c also can be determined so as to relate the position of the tracked instrument 5 to the "virtual camera".

Figure 2:
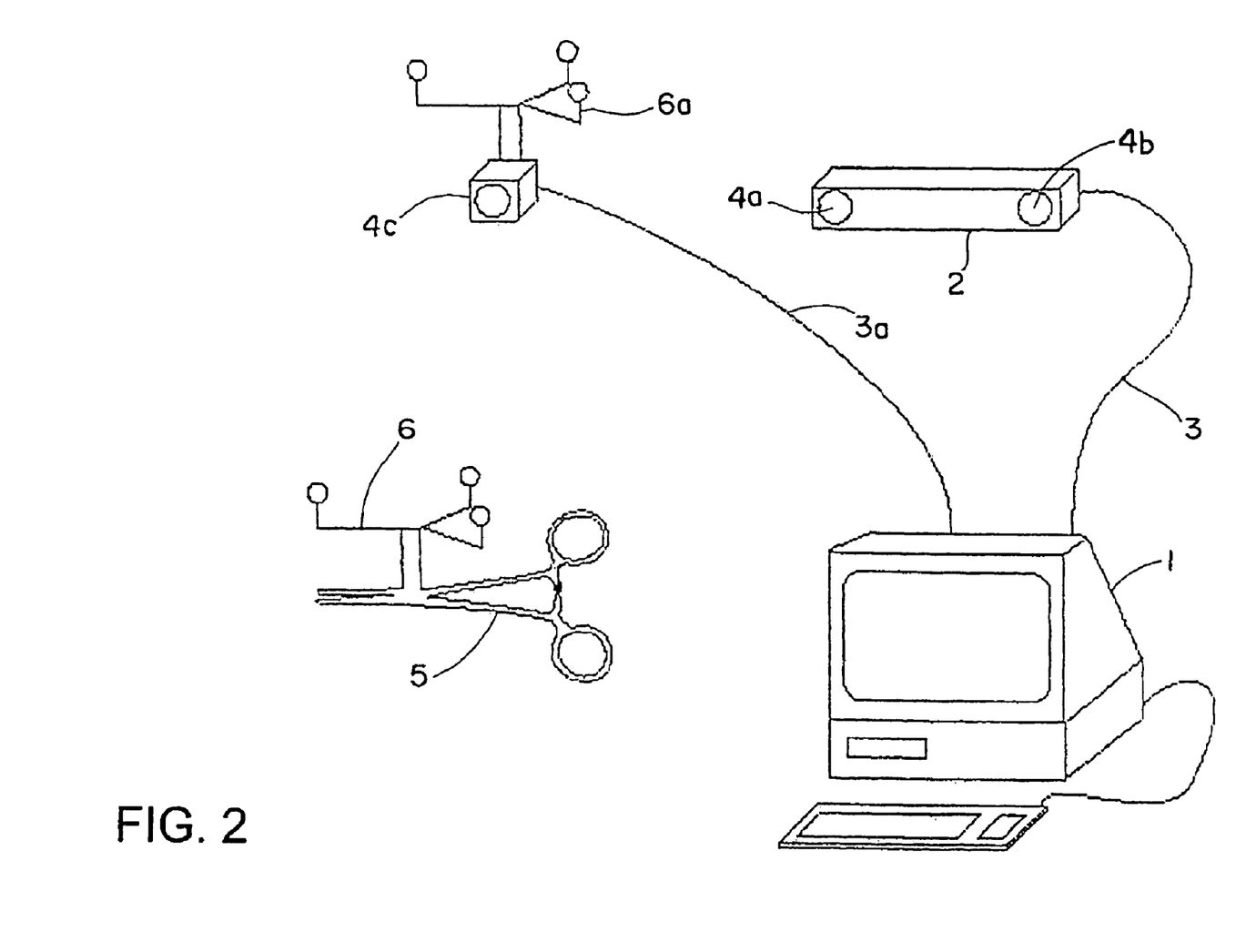
FIG. 2 illustrates another exemplary device in accordance with the invention.

FIG. 2 shows a second embodiment, wherein another camera 4c is detached from the optical tracking system 2 (which includes the cameras 4a and 4b). The camera 4c can be connected to the computational unit 1 via a separate data connection, such as for example a cable 3a. Such an arrangement enables detection of the instrument 5 to be more flexibly configured using the additional camera 4c, since the latter can be positioned independent of the tracking system 2. This can enable easy detection of the instrument 5 from a number of directions. To this end, the distance, starting from the coordinate system of the additional camera 4c, between the instrument 5 and the camera 4c can be ascertained. This enables evaluation of the image data detected by the camera 4c such that dimensions or the geometry of the instrument 5 can be ascertained from the data. A spatial location of the camera 4c, via its connection reference star 6a (which is detectable by the tracking system 2) can be calculated. From the spatial position of the additional camera 4c, the relative position between the camera 4c and the instrument 5 also can be calculated. Thus, the distance between the instrument 5 and the video cameras can be determined. It is thus for example possible to calibrate an instrument by means of three cameras 4a, 4b and 4c, which can respectively detect infrared and visible light.

Figure 3:
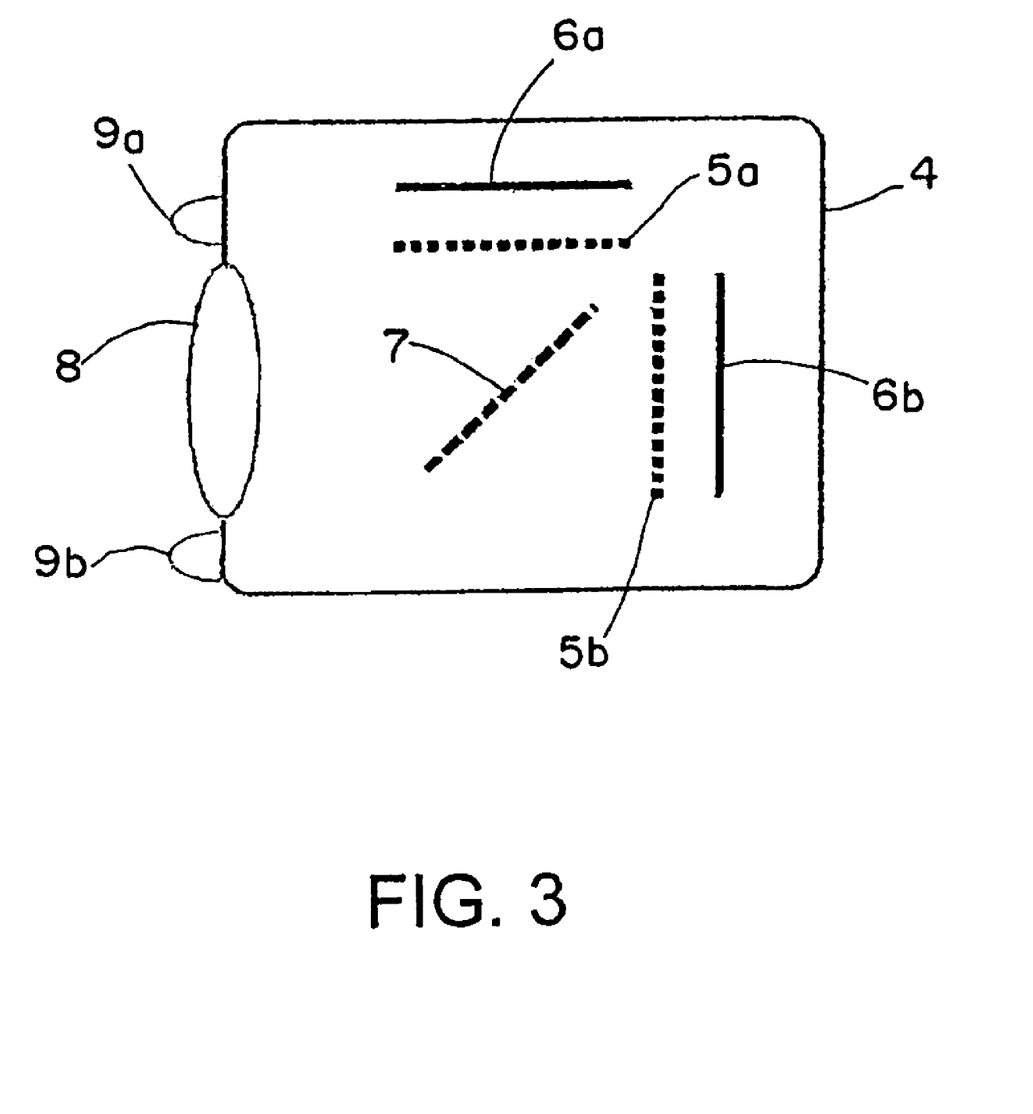
FIG. 3 is a schematic cross-sectional view of an exemplary camera of a camera system in accordance with the invention, said camera system used in accordance with the device of FIG. 1.
Figure 5:
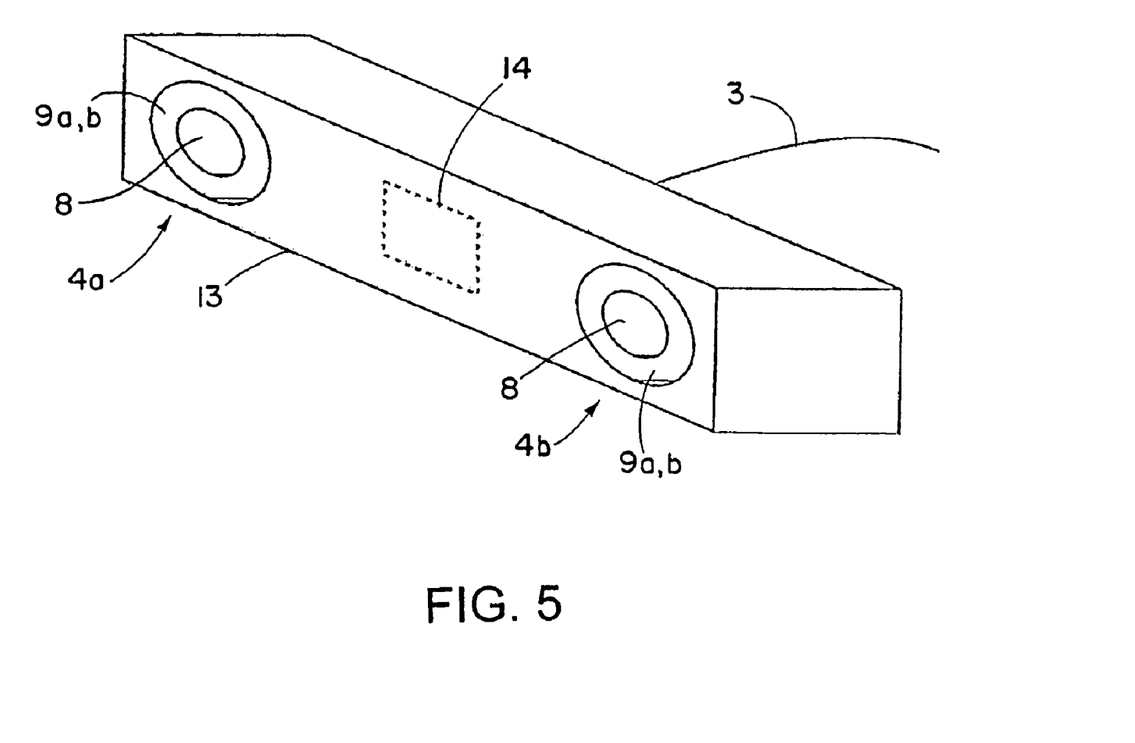
FIG. 5 is a perspective view of an exemplary stereoscopic camera in accordance with the invention.

FIG. 3 shows a perspective cross-sectional view of a camera 4, wherein in the incident light region of the camera 4, a lens 8 is shown as an example of a lens system and is surrounded by LEDs 9a and 9b. The LEDs 9a and 9b, for example, can be arranged annularly around the lens 8 as shown in FIG. 5. A beam of light entering through the lens system or lens 8 impinges on a semi-transparent mirror 7, which lets through a portion of the beam of light so as to strike both the filter 5b lying directly in the beam path and the detection element or CCD element 6b lying behind it. By means of the CCD element 6b, light can be detected in the wavelength range which the filter 5b lets through. A portion of the light entering through the lens 8 also may be reflected by the semi-transparent mirror 7 in the direction of the second filter 5a, which lets through light in a different wavelength range relative to the filter 5b. The light of said other wavelength range strikes the second CCD element 6a lying behind the filter 5a in the direction of the beam of light reflected by the semi-transparent mirror 7, wherein said CCD element 6a can detect in said other wavelength range. The wavelength range that is detected, sequentially or also simultaneously, by the CCD elements 6a and/or 6b can be set, depending on the type of filters 5a and 5b that are used.

It may be noted that one of the filters 5a and 5b can be omitted in the example embodiment shown in FIG. 3. This can be done, for example, to detect visible light by means of the CCD element not shielded by a filter, wherein an infrared filter, for example, can be placed in front of the other CCD element.

The region in front of the camera 4, for example, can be illuminated with infrared light by means of a light source 9a. This can improve the detection of reflective markers. The second light source 9b, for example, can emit light in another wavelength range, such as for example visible light or also ultraviolet light, so as to improve the detection of objects using light in the visible range. However, depending on the application, it is also possible to omit one or all of the illuminating elements 9.

It may be noted that the position of the CCD elements 6a and 6b in relation to the semi-transparent mirror 7 can be different. For example, the CCD elements 6a and 6b can be at different distances from the mirror 7, since light of different wavelengths does not focus onto exactly the same point. The optical element 8 can also be configured to be variable, in a similar way for example to a photographic or video camera such as is known in its own right, in order to focus the light on the respective sensor 6a or 6b, depending on the desired light detection range.

Figure 4:
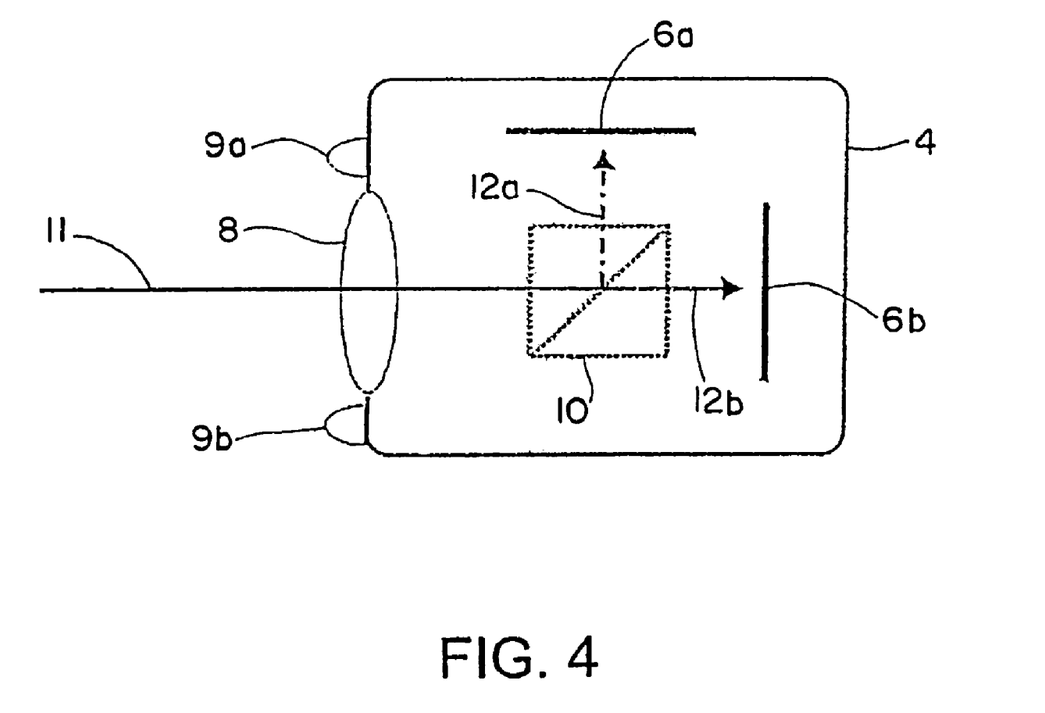
FIG. 4 is a schematic cross-sectional view of another exemplary camera of a camera system in accordance with the invention, said camera system used in accordance with the device of FIG. 2.

FIG. 4 shows a second embodiment of a camera 4 in accordance with the invention, wherein a beam splitting prism 10 is provided instead of the semi-transparent mirror 7 shown in FIG. 3. Light 11 entering the prism 10 is split into light of a first wavelength range 12b, which passes through the prism 10 and strikes the first CCD element 6b. Light of a second wavelength range can be refracted by the prism 10 and deflected onto the second CCD element 6a as diverted light 12a. It is thus also possible to omit filters and simultaneously, for example continuously, detect an object using the two CCD elements 6a and 6b.

FIG. 5 shows an exemplary stereoscopic camera, wherein two individual cameras 4a and 4b are separated from one another, for example as described above, are arranged in a casing 13. The respective lenses 8 and the illuminating elements or LEDs 9 can be seen in the perspective shown in FIG. 5. A CPU 14 can be arranged in the casing 13 and connected to each of the cameras 4a and 4b and, in particular, to the respective CCD elements 6a and 6b. Via a connection 3, stereoscopic images detected by the cameras 4a and 4b can be transmitted in two different wavelength ranges to the computational unit 1 shown in FIGS. 1 and 2.

Recording the images using the cameras 4a and 4b, setting the lens system 8 or setting or positioning a filter 5a and 5b, such as for example shifting a filter in front of one or more of the CCD elements 6a and 6b in order to detect a different wavelength range, can be controlled by means of the computational unit or CPU 14. The CPU 14 also can synchronize the CCD elements 6a and 6b of a camera and the illuminating elements 9a and 9b respectively assigned to the respective CCD elements 6a and 6b. The evaluation result or also the optical signals, which for example may not be directly evaluated by the CPU 14, can be transmitted to another system via the connection 3.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A tracking camera system configured to determine a location of an object in three dimensional space, the tracking camera system comprising:
    at least two camera units, each camera unit including at least one detection element for detecting an optical signal; wherein
    at least one camera unit of the at least two camera units includes at least one element operative to enable the at least one camera unit's detection element to detect optical signals in at least two different spectral ranges wherein the at least one element comprises at least one optical filter having a settable filter characteristic, wherein based on the settable filter characteristic, optical signal entering the at least one camera unit is subjected to different filter characteristics.

2. The camera system according to claim 1, wherein the at least one element comprises at least one optical filter arranged in front of the at least one detection element.

3. The camera system according to claim 1, wherein at least one camera unit includes at least two detection elements.

4. The camera system according to claim 3, wherein the at least one element comprises a deflection element for deflecting optical signals entering the at least one camera unit onto the at least two detection units.

5. The camera system according to claim 4, wherein the deflection element deflects at least a partial spectrum of optical signals or optical signals of a particular wavelength onto at least one of the at least two detection elements.

6. The camera system according to claim 4, wherein the deflection element is a semi-transparent mirror or a prism.

7. The camera system according to claim 1, wherein the at least one detection element is an electronic detection element, a CCD chip, CMOS sensor, a line sensor or a sensor array.

8. The camera system according to claim 1, wherein the at least one element is a movable mirror.

9. The camera system according to claim 1, wherein the at least one element comprises at least one optical filter having a settable filter characteristic, wherein based on the settable filter characteristic, optical signals entering the at least one camera unit is subjected to different filter characteristics.

10. The camera system according to claim 1, wherein each camera unit comprises an optical system through which optical signals enter the respective camera unit.

11. The camera system according to claim 10, wherein the optical system comprises a lens.

12. The camera system according to claim 11, wherein the optical system is a settable or variable optical system.

13. A navigation system comprising a camera system according to claim 1.

14. The camera system according to claim 1, further comprising a processing device configured to determine the location of the object in three-dimensional space based on data collected by the respective detection elements.

15. The camera system according to claim 1, wherein the at least two different spectral ranges comprise at least one of a) visible light and infrared light, b) visible light and ultraviolet light, or c) infrared light and ultraviolet light.

* * * * *